United States Patent [19]
Sebald

[11] Patent Number: 5,723,118
[45] Date of Patent: Mar. 3, 1998

[54] THERAPEUTIC AGENTS WHICH ARE ANTAGONISTS OR PARTIAL AGONISTS OF HUMAN INTERLEUKIN 4

[75] Inventor: Walter Sebald, Würzburg, Germany

[73] Assignee: Bayer Aktiengesellschaft, Leverkusen, Germany

[21] Appl. No.: 232,289

[22] PCT Filed: Nov. 13, 1992

[86] PCT No.: PCT/EP92/02614

§ 371 Date: May 6, 1994

§ 102(e) Date: May 6, 1994

[87] PCT Pub. No.: WO93/10235

PCT Pub. Date: May 27, 1993

[30] Foreign Application Priority Data

Nov. 13, 1991 [DE] Germany ............... 41 37 333.2

[51] Int. Cl.$^6$ .................. C07K 14/54; A61K 38/20
[52] U.S. Cl. ............ 424/85.2; 435/7.21; 435/69.52; 435/252.3; 435/320.1; 530/351; 514/12
[58] Field of Search ............... 514/12; 530/324, 530/351; 435/69.52, 252.3, 320.1, 172.3, 7.21; 424/85.2

[56] References Cited

U.S. PATENT DOCUMENTS

| | | | |
|---|---|---|---|
| 5,017,691 | 5/1991 | Lee et al. ............... | 535/351 |
| 5,188,827 | 2/1993 | Black ..................... | 424/85.2 |

FOREIGN PATENT DOCUMENTS

| | | |
|---|---|---|
| 0314402 | 5/1989 | European Pat. Off. . |
| 0327283 | 8/1989 | European Pat. Off. . |

OTHER PUBLICATIONS

Craig D. Wegner et al., "intercellular Adhesion Molecule–1(ICAM–1) in the Pathogenesis of Asthma" *Science*, 247:456(1990).

Robert H. Gundel et al., "Antigen–coated Sepharose Beads Induce Airway Eosinophilia and Airway Hyperresponsiveness in Cynomolgus Monkeyts", *Am.Rev. Respir.Dis.*, 140:629(1989).

Robert H. Gundel et al., "The Effects of a 5–Lipoxygenase Inhibitor on Antigen–Induced Mediator Release, Late Phase Bronchoconstriction and Cellular Infiltrates in Primates", *Adv.Prost. Throm.Leuko.Res.*, 21:457(1990).

Robert H. Gundel et al., "Repeated Antigen Inhalation Results in a Prolonged Airway Eosinophilia and Airway Hyperresponsiveness in Primates", *J.Appl. Physiol.*, 68:779(1990).

Robert H. Gundel et al., "Antigen–induced Acute and Late–phase Responses in Primates", *Am.Rev.Respir.Dis.*, 146:369(1992).

Robert H. Gundel et al., "Antigen–induced Mediator Release in Primates", *Am.Rev.Respir.Dis.*, 144:76(1991).

Robert H. Gundel et al., "The Onset and Recovery from Airway Hyperresponsiveness: Relationship with Inflammatory Cell Infiltrates and Release of Cytotoxic Granule Proteins", *Clin.Exp.All.*, 22: 303(1992).

Robert H. Gundel et al., "Adhesion Molecules and the Modulation of Mucosal Inflammation", in *Immunopharmacology of Epithelial Barriers*, Academic Press Ltd., Chapter 3 (1994).

Robert H. Gundel et al., "Eosinophils and Neutrophils in a Primate Model of Asthma", in Asthma: Physiology, *Immunopharmacology, and Treatment, Fourth International Symposium*, Academic Press Ltd., Chapter 14(1993).

David J. Fraenkel et al., "Etiology of Asthma: pathology and Mediators", in *Allergy, Asthma, and Immunology from Infancy to Adulthood*. Third Edition, C.W. Bierman et al., editors, W.B. Saunders Co., Philadelphia, 1996, p. 446.

N. Kruse et al., *EMBO J.*, 11: 3237–3244 (1992).

N. Kruse et al., *EMBO J.*, 12: 5121–5129 (1993).

H. Tony et al., *Eur. J. Biochem.*, 225: 659–665 (1994).

Konda et al., *Science*, 262: 1874–1877.

Russell et al., *Science*, 262: 1880–1883.

(1) Kruse, N. et al., FEBS Letters (1991), vol. 286, No. 1, 2, pp. 58–60.

(2) Kikutani, H. et al., Cell (1986), vol. 47, pp. 657–665.

(3) Carr, C. et al., Biochemstry (1991), vol. 30, pp. 1515–1523.

(4) Kramer et al., Nucleic Acids Research (1984), vol. 12, pp. 9441–9455.

(5) Kramer et al., Cell (1984), vol. 38, pp. 879–887.

(6) Boehringer Mannheim Prospekt, Biochemicals for Molecular Biology (1987), pp. 35–38.

(7) McCarthy et al., Gene (1986), vol. 41, pp. 201–206.

(8) Kato et al., Biochem. Biophys. Res. Commun. (1985), vol. 130, pp. 692–699.

(9) Schauder et al., Gene (1987), vol. 52, pp. 279–283.

(10) Arai K.I. et al., Annu. Rev. Biochem (1990), vol. 59, pp. 783–836.

(11) Finkelman, F.D. et al., (1990) Annu. Rev. Immunol., vol. 8, pp. 303–333.

(12) Yokota, T. et al., Immunol. Rev., vol. 102, pp. 137–187 (1988).

(13) Idzerdas, R.L. et al., J. Exp. Med. (1990), vol. 171, pp. 861–873.

(14) Cosman, D. et al., Trends Biochem. Sci., vol. 15, pp. 265–270 (1990).

(15) Yokota, T. et al., Proc. Natl. Acad. Sci., USA (1986), pp. 5894–5898.

(List continued on next page.)

*Primary Examiner*—Stephen Walsh
*Assistant Examiner*—Prema Mertz
*Attorney, Agent, or Firm*—Sprung Kramer Schaefer & Briscoe

[57] ABSTRACT

The invention relates to therapeutic agents which are antagonists or partial agonists of human interleukin 4, or contain these antagonists or partial agonists, to mutant hIL-4 proteins and to processes for their preparation.

21 Claims, No Drawings

OTHER PUBLICATIONS

(16) van Kimmenade, A. et al. (1988), Eur. J. Biochem., vol. 173, pp. 109–114.

(17) Jayaram, B. et al., Gene (1989), vol. 79, pp. 345–354.

(18) Solari, R. et al. (1989) Biochem. J., vol. 262, pp. 897–908.

(19) Weigel, U. et al., Eur. J. Biochem. (1989), vol. 180, pp. 295–300.

(20) EMBO Journal, Kruse, N. et al., vol. 11, No. 9, 1992, pp. 3237–3244.

(21) European Journal of Biochemistry, vol. 180, 1989, pp. 295–300.

(22) Biological Chemistry Hoppe–Seyler, vol. 373, No. 9, 1992, pp. 789–790.

THERAPEUTIC AGENTS WHICH ARE ANTAGONISTS OR PARTIAL AGONISTS OF HUMAN INTERLEUKIN 4

Therapeutic agents which are antagonists or partial agonists of human interleukin 4, or contain these antagonists or partial agonists, and mutant hIL-4 proteins, as well as processes for their preparation Broad sectors of the population suffer nowadays from allergies. The increasing pollution of the air and the increase in number of allergy-eliciting substances which are diffused within the environment make it probable that the number of cases will increase still further in the future, particularly in children. For this reason, it is urgently necessary to develop medicaments which can intervene in the course of allergic processes.

Human interleukin 4 (hIL-4) is one of the numerous cytokines which induce and coordinate the proliferation, the maturation, the survival and the differentiation of lymphoid and myeloid cells (1–3). In particular, hIL-4 participates in the IgE-mediated immune reaction and directly accelerates the proliferation of thymocytes and activated T cells. It has been possible to identify a high-affinity IL-4 receptor protein of Mr 140,000 which, according to its cDNA sequence, consists of 800 amino acid residues (4). This protein belongs to a recently described group of receptors which are designated the haematopoietin receptor superfamily (5).

Based on the cloned cDNA (6), the amino acid sequence of the mature IL-4 consists of 129 residues. The cDNA has been expressed in *E. coli* (7, 8) and yeast (9). Recombinant IL-4 possessing a high level of biological activity can be isolated from these sources.

The role of interleukin 4 in allergic processes makes it seem likely that substances which inhibit interleukin-4-mediated processes, or compete with hIL-4, will interrupt the disease-eliciting reaction chain.

It is, therefore, the object of the invention to make available therapeutic agents whose active constituents are antagonists or partial agonists of human interleukin 4.

Very recently, a monoclonal antibody has become known which exhibits antagonistic properties towards human interleukin 4 (10). This antibody contains a Fab fragment and is produced by a human-human hybridoma cell line. In addition, a hybridoma cell line from the spleen cells of a rat immunized against (non-)glycosylated human IL-4 produces monoclonal antibodies against hIL-4 (11).

The stated object was achieved, in accordance with the present invention, by making available therapeutic agents which are antagonists or partial agonists of hIL-4, or which contain these antagonists or partial agonists, and are characterized in that the antagonists or partial agonists are mutant hIL-4 proteins. The choice of the therapeutic agents according to the invention has the advantage that "genetic engineering" can be used, in a targeted manner, to prepare proteins which, due to their similarity to the wild-type hIL-4, compete with the latter for occupation of the hIL-4 receptor.

In addition, it is an object of the invention to make available mutant hIL-4 proteins as well as processes for their preparation.

hIL-4 can be produced as a recombinant protein (rhIL-4) by genetic manipulation, e.g. in *E. coli*. The protein which is formed under these circumstances can be solubilized, renatured and isolated. The rhIL-4 then possesses a high level of specific biological activity, which can be determined, for example, by measuring the DNA synthesis/proliferation of activated T cells, or the CD23 expression of activated B cells (see, e.g., Kruse, N. et al. (1991) FEBS Lett. 286, 58–60; Kikutani, H. et al. (1986) Cell 47, 657–665).

In accordance with the invention, a process has now been designed by which mutant proteins of the hIL-4 wild type can be produced, which proteins possess the properties of hIL-4 antagonists or partial hIL-4 agonists. The antagonists of hIL-4, in particular, offer the possibility of specifically inhibiting the effect of hIL-4. For this purpose cDNA, which contains a DNA region which encodes the mature region of hIL-4, is subjected to a targeted oligonucleotide mutagenesis (site-directed mutagenesis) such that a selected different amino acid of the possible natural amino acids, is expressed at the desired position(s), or that an interruption of the polypeptide chain is produced by a stop codon, the DNA region which encodes the mutated, mature region of hIL-4 is integrated into an expression vector, the hybrid vector which has been formed is inserted into *E. coli*, and the mutant hIL-4 protein is expressed and, where appropriate, isolated.

With regard to the procurement of cDNA which contains a DNA region which encodes the mature region of hIL-4, or which encodes the mature region of hIL-4, reference is made to (6) and the literature listed therein. In the present context, "cDNA which encodes the mature region of hIL-4" is also understood to mean cDNAs which, while having an approximately equal number of base pairs, represent mutants of the cDNA which is specifically indicated in the said state of the art, provided that the hIL-4 muteins which are thereby to be designated are also antagonists or partial agonists.

The numbering of the DNA region encoding the mature region of hIL-4 follows that of Garr, C. et al. (Biochemistry (1991) 30, 1515–1523).

cDNA which encodes the mature region of hIL-4 can be obtained by cutting out an EcoRV/BamHI fragment from a cDNA which has been prepared by genetic manipulation (e.g. from British Bio-Technology Ltd., Oxford, England).

The DNA fragment is integrated, with the addition of synthetic oligonucleotides, e.g. 5'-CATGCACAAGTGCGAT (SEQ ID NO: 1) and 5'-ATCGCACTTGTG, (SEQ ID NO: 2) which contain the first 4 amino acid codons of interleukin 4 and also the codon for the initiating methionine, into an expression vector, for example between the NcoI and BamHI cleavage sites of the expression vector $R^{TS}$ pRC 109 (12).

The site-directed mutagenesis can be carried out in accordance with Kramer et al. (Nucleic Acids Research (1984) 12, 9441–9455; Cell (1984) 38, 879–887; and Boehringer-Mannheim catalogue, Biochemicals for Molecular Biology (1987) 35 etc., see also (12)). The oligonucleotide used for the mutagenesis can contain some 6 to 10 bases upstream of and some 6 to 10 bases downstream of the base(s) to be altered.

The person skilled in the art is also familiar with excision of the DNA region encoding the mutated, mature region of hIL-4 from the vector, transfer of this DNA region into an expression vector, subsequent insertion of the expression vector into *E. coli*, as well as expression of the mutant hIL-4 protein and its facultative isolation (McCarthy et al.; Gene (1986) 41, 201–206; Karo et al.; Biochem. Biophys. Res. Commun. (1985) 130, 692–699), in association with which modifications (12) are possible.

In accordance with a special embodiment of the process according to the invention, DNA encoding an initiating methionine is incorporated into the cDNA which contains the DNA region which encodes the mature region of hIL-4 prior to the site-directed mutagenesis being carried out.

In accordance with a further special embodiment, the DNA region which encodes the mutated, mature region of hIL-4 can be excised from the cDNA mutant as a NcoI/BamHI fragment.

For the expression, use is preferably made of a temperature-regulated expression vector, for example pILA502 (without left-hand lambda promoter and polylinker) and/or a common *E. coli* strain as the host, for example JM103 (recA⁻). With regard to pILA502, compare Schauder et al. (Gene (1987) 52, 279–283). Further suitable expression systems can be obtained from Pharmacia ("Prokaryotic Gene Fusion Vectors"). The *E. coli* strain JM103 can also be obtained from Pharmacia.

In accordance with a further embodiment, the invention relates to an hIL-4 mutant of the wild type, in which mutant Tyr is replaced by Asp in the region of position 124.

The invention is explained in more detail below with the aid of two examples.

EXAMPLE 1 cDNA, which encoded the mature region of hIL-4 end an initiating methionine, was subjected to site-directed mutagenesis in accordance with Kramer et al. The synthetic oligonucleotide contained 6 bases upstream and downstream of the nucleotide to be replaced and was prepared with the aid of a DNA synthesizer (Applied Biosystems, Model 380). The site to be replaced was position 124 in the C-terminal, probably α-helical, region (positions 110 to 129). In this case, Tyr was replaced by Gly. The resulting mutation was verified by DNA sequence analysis of single-stranded bacteriophage DNA. The mutated cDNA was excised as a NcoI/BamHI fragment from the double-stranded viral DNA and combined with a temperature-regulated expression vector which corresponded to pILA502 except that the left-hand lambda promoter and the polylinker were lacking. A recA⁻ derivative of the *E. coli* strain JM103 was used as the host. The integrated hIL-4 cDNA was sequenced in order to confirm the mutation. After that, the strain was employed for expressing the mutein.

Following expression and isolation, it was found that the mutein (Y124G) binds with unchanged affinity to the receptor for hIL-4. However, the maximum inducible proliferation of activated peripheral T cells is now only 10–20% of the proliferation which is inducible by hIL-4 wild type. This shows that mutein Y124G possesses the properties of a partial agonist.

EXAMPLE 2

Example 1 was repeated except that Asp was expressed at position 124 instead of Tyr. Even at a concentration of 1 μM, the isolated mutein Y124D shows no activity against activated peripheral T cells. However, it inhibits the activity of the hIL-4 wild type with an inhibitor constant of about 600 pM. This shows that mutein Y124D has the properties of an antagonist. Mutein Y124D has a small residual activity with regard to the induction of CD23 on activated B cells. However, the maximum achievable induction is only about 5% of the induction which can be achieved with the hIL-4 wild type. In this system, the activity of the hIL-4 wild type is inhibited by mutein Y124D with an inhibitor constant $K_i$ of about 800 pM. Thus, in the B cell system, mutein Y124D has the properties of a very weak agonist.

EXAMPLE 3

Example 1 was repeated except that Asp was expressed at position 121 instead of Arg. The binding of the isolated mutein to the hIL-4 receptor was unchanged. However, the maximum proliferation of activated peripheral T cells which could be induced was only about 30% of the proliferation which was inducible with hIL-4 wild type. This shows that mutein R121D possesses the properties of a partial agonist.

EXAMPLE 4

Example 1 was repeated except that Asp was expressed at position 125 instead of Set. The isolated mutein S125D bound with unchanged affinity to the receptor for hIL-4. However, the maximum proliferation of activated peripheral T cells which can be induced is only about 35% of the proliferation which is inducible with hIL-4 wild type.

Literature list:
1) Arai, K. I., Lee, F., Miyajima, A., Miyatake, S., Arai, N. and Yokota, T. (1990) Annu. Rev. Biochem. 59, 783–836.
2) Finkelman, F. D., Holmes, J., Katona, I. M., Urban, J. F., Beckmann, M. P., Park, L. S., Schooley, K. A., Coffman, R. L., Mosmann T. R. and Paul, W. E. (1990) Annu. Rev. Immunol. 8, 303–333.
3) Yokota, T., Arai, N., De Vries, J., Spits, H., Banchereau, J., Zlotnik, A., Rennick, D., Howard, M., Takebe, Y., Miyatake, S., Lee, F. and Arai, K. I. (1988) Immunol Rev. 102, 137–187.
4) Idzerda, R. L., March, C. J., Mosley, B., Lyman, S. D., Vanden Bos, T., Gimpel, S. D., Din, W. S., Grabstein, K. H., Widmer, M. B., Park, L. S., Cosman, D. and Beckmann, M. P. (1990) J. Exp. Med. 171, 861–873.
5) Cosman, D., Lyman, S .D., Idzerda, R. L., Beckmann, M. P., Park, L. S., Goodwin, R. G. and March, C. J. (1990) Trends Biochem. Sci. 15, 265–270.
6) Yokota, T., Otsuka, T., Mosmann T., Banchereau, J., DeFrance, T., Blanchard, D., De Vries, J. E., Lee, F. and Arai, K. I. (1986) Proc. Natl. Acad. Sci. USA 83, 5894–5898.
7) Van Kimmenade, A., Bond, M. W., Schumacher, J. H., Laquoi, C. and Kastelein, R. A. (1988) Eur. J. Biochem. 173, 109–114.
8) Jayaram, B., Bevos, R., Guisez, Y. and Fiers, W. (1989) Gene 79, 345–354.
9) Solari, R., Quint, D., Obray, H., McNamee, A., Bolton, E., Hissey, P., Champion, B., Zanders, E., Chaplin, A., Coomber, B., Watson, M., Roberts, B. and Weir, M. (1989) Biochem. J. 262, 897–908.
10) Coffman, R. L.; de Vries, J. E. (Schering Biotech Corp., USA), EP 327283 A1.
11) Abrams, J. S.; Chretien, I.; Lee, F. D.; Pearce, M. K. (Schering Biotech Corp., USA), EP 314402 A2.
12) Weigel, U., Meyer, M. and Sebald, W. (1989) Eur. J. Biochem. 180, 295–300.

I claim:

1. A mutant human interleukin-4 (hIL-4) protein, said mutant hIL-4 protein having the amino acid sequence of wild type hIL-4 protein, but wherein one or more of the amino acids occurring therein at positions 121, 124 or 125 is replaced by another natural amino acid, or the amino acid sequence is terminated at one of these positions, with the exception of mutein tyrosine124aspartic acid, said mutant hIL-4 protein being an antagonist or partial agonist of hIL-4-mediated in vitro T-cell proliferation.

2. The mutant hIL-4 protein according to claim 1, wherein said mutant hIL-4 protein has the amino acid sequence of wild type hIL-4 protein, but wherein the amino acid tyrosine, which occurs naturally at position 124, is replaced by another natural amino acid except aspartic acid.

3. The mutant hIL-4 protein according to claim 2, wherein said tyrosine is replaced by glycine.

4. The mutant hIL-4 protein according to claim 1, wherein said mutant hIL-4 protein has the amino acid sequence of wild type hIL-4 protein, but wherein the amino acid arginine, which occurs naturally at position 121, is replaced by another natural amino acid.

5. The mutant hIL-4 protein according to claim 4, wherein said arginine is replaced by aspartic acid.

6. The mutant hIL-4 protein according to claim 1, wherein said mutant hIL-4 protein has the amino acid sequence of wild type hIL-4 protein, but wherein the amino acid serine, which occurs naturally at position 125, is replaced by another natural amino acid.

7. The mutant hIL-4 protein according to claim 6, wherein said serine is replaced by aspartic acid.

8. A therapeutic agent comprising:

(a) a mutant human interleukin-4 (hIL-4) protein according to claim 1; and (b) a physiologically acceptable carrier.

9. The therapeutic agent according to claim 8, wherein said mutant hIL-4 protein has the amino acid sequence of wild type hIL-4 protein, but wherein the amino acid tyrosine, which occurs naturally at position 124, is replaced by another natural amino acid except aspartic acid.

10. The therapeutic agent according to claim 9, wherein said tyrosine is replaced by glycine.

11. The therapeutic agent according to claim 8, wherein said mutant hIL-4 protein has the amino acid sequence of wild type hIL-4 protein, but wherein the amino acid arginine, which occurs naturally at position 121, is replaced by another natural amino acid.

12. The therapeutic agent according to claim 11, wherein said arginine is replaced by aspartic acid.

13. The therapeutic agent according to claim 8, wherein said mutant hIL-4 protein has the amino acid sequence of wild type hIL-4 protein, but wherein the amino acid serine, which occurs naturally at position 125, is replaced by another natural amino acid.

14. The therapeutic agent according to claim 13, wherein said serine is replaced by aspartic acid.

15. A method of antagonizing or partially agonizing the effect of human interleukin-4 (hIL-4) comprising contacting cells expressing the hIL-4-receptor with an antagonistic or partially agonistic effective amount of a mutant hIL-4 protein according to claim 1.

16. The method according to claim 15, wherein said mutant hIL-4 protein has the amino acid sequence of wild type hIL-4 protein, but wherein the amino acid tyrosine, which occurs naturally at position 124, is replaced by another natural amino acid except aspartic acid.

17. The method according to claim 16, wherein said tyrosine is replaced by glycine.

18. The method according to claim 15, wherein said mutant hIL-4 protein has the amino acid sequence of wild type hIL-4 protein, but wherein the amino acid arginine, which occurs naturally at position 121, is replaced by another natural amino acid.

19. The method according to claim 18, wherein said arginine is replaced by aspartic acid.

20. The method according to claim 15, wherein said mutant hIL-4 protein has the amino acid sequence of wild type hIL-4 protein, but wherein the amino acid serine, which occurs naturally at position 125, is replaced by another natural amino acid.

21. The method according to claim 20, wherein said serine is replaced by aspartic acid.

* * * * *

SEQUENCE LISTING ( 1 ) GENERAL INFORMATION:

( i i i ) NUMBER OF SEQUENCES: 2

-continued ( 2 ) INFORMATION FOR SEQ ID NO: 1:

( i ) SEQUENCE CHARACTERISTICS:
( A ) LENGTH: 16 nucleotides
( B ) TYPE: Nucleic acid
( C ) STRANDEDNESS: Single
( D ) TOPOLOGY: Linear ( x i ) SEQUENCE DESCRIPTION: SEQ ID NO:1:

CATGCACAAG TGCGAT 16

( 2 ) INFORMATION FOR SEQ ID NO: 2:

( i ) SEQUENCE CHARACTERISTICS:
( A ) LENGTH: 12 nucleotides
( B ) TYPE: Nucleic acid
( C ) STRANDEDNESS: Single
( D ) TOPOLOGY: Linear ( x i ) SEQUENCE DESCRIPTION: SEQ ID NO:2:

ATCGCACTTG TG 12